(12) United States Patent
Bindrim

(10) Patent No.: US 8,017,092 B2
(45) Date of Patent: Sep. 13, 2011

(54) ANALYZER AND REAGENT CONTAINER

(75) Inventor: Karl-Heinz Bindrim, Hamburg (DE)

(73) Assignee: Sysmex Corporation, Kobe (JP)

( * ) Notice: Subject to any disclaimer, the term of this patent is extended or adjusted under 35 U.S.C. 154(b) by 1032 days.

(21) Appl. No.: 11/013,993

(22) Filed: Dec. 16, 2004

(65) Prior Publication Data

US 2005/0191211 A1 Sep. 1, 2005

(30) Foreign Application Priority Data

Dec. 16, 2003 (EP) .................................... 03028679

(51) Int. Cl.
*B01L 3/00* (2006.01)

(52) U.S. Cl. ........ 422/544; 422/538; 422/555; 422/547; 422/68.1; 422/500; 604/408; 604/403; 604/257; 604/245; 604/153

(58) Field of Classification Search ................... 422/63, 422/68.1, 99, 102, 103, 944; 604/33, 152, 604/153, 213, 245, 250, 256, 257, 326, 403, 604/408

See application file for complete search history.

(56) References Cited

U.S. PATENT DOCUMENTS

| | | | | |
|---|---|---|---|---|
| 3,729,023 A | * | 4/1973 | Hammond | 137/614.03 |
| 3,851,666 A | * | 12/1974 | Hammond | 137/614.04 |
| 3,953,136 A | * | 4/1976 | Hach | 356/410 |
| 4,745,950 A | * | 5/1988 | Mathieu | 137/798 |
| 4,889,527 A | * | 12/1989 | Herrli | 604/29 |
| 5,570,815 A | * | 11/1996 | Ramsay | 222/95 |
| 5,665,315 A | | 9/1997 | Robert et al. | |
| 5,743,878 A | * | 4/1998 | Ross et al. | 604/131 |
| 6,250,130 B1 | * | 6/2001 | Howard et al. | 73/1.36 |
| 2002/0020449 A1 | | 2/2002 | Imai | |

FOREIGN PATENT DOCUMENTS

| | | |
|---|---|---|
| DE | 19914536 | 10/2000 |
| JP | 63-099852 A | 6/1988 |
| JP | 04-145289 A | 5/1992 |
| JP | 06-273425 | 9/1994 |
| JP | 08-278235 | 10/1996 |
| JP | 09-051945 A | 2/1997 |
| JP | 09-297146 | 11/1997 |
| WO | WO 01/49415 A2 | 7/2001 |

* cited by examiner

*Primary Examiner* — Jill Warden
*Assistant Examiner* — Cedric Chan
(74) *Attorney, Agent, or Firm* — Brinks Hofer Gilson & Lione

(57) ABSTRACT

An analyzer enabling the user to hardly breathe in a malodor given off from a reagent when exchanging a reagent container is obtained. This analyzer, connected with a reagent container including a flexible container body storing the reagent, comprises an analyzer body analyzing an analyte with the reagent and reagent transporter having a first end connected to the analyzer body and a second end connected to the reagent container. The reagent transporter includes a first connectional part, detachably connected to the reagent container, having a first switching member forming and blocking a first passage between the analyzer body and the reagent container, while the first switching member blocks the first passage when the first connectional part is separated from the reagent container, and forms the first passage when the first connectional part is connected to the reagent container.

5 Claims, 9 Drawing Sheets

ANALYZER AND REAGENT CONTAINER

RELATED APPLICATIONS

This application claims priority under 35 U.S.C. § 119 to European Patent Application No. 03028679.3, filed Dec. 16, 2003.

BACKGROUND OF THE INVENTION

1. Field of the Invention

The present invention relates to an analyzer and a reagent container, and more particularly, it relates to an analyzer analyzing an analyte with a reagent and a reagent container.

2. Description of the Background Art

A structure obtained by connecting a reagent container for storing an analytical reagent employed in a clinical test apparatus with the clinical test apparatus through a tube is known in general. Such a structure is disclosed in Japanese Patent Laying-Open No. 9-297146 (1997), for example. In the structure disclosed in Japanese Patent Laying-Open No. 9-297146, a flexible tube is connected to an opening of the reagent container, in which a suction pipe is arranged. The suction pipe sucks the reagent stored in the reagent container for supplying the sucked reagent to the clinical test apparatus through the tube mounted on the opening of the reagent container.

When the reagent is almost used up and the tube is detached from the reagent container for exchanging the same in the aforementioned structure disclosed in Japanese Patent Laying-Open No. 9-297146, however, the reagent partially remaining in the reagent container or the tube disadvantageously comes into contact with the air. If the reagent coming into contact with the air is a reagent hemolyzing blood cells which is giving off a malodor, for example, the user of the reagent disadvantageously breathes in such a malodor when exchanging the reagent container.

SUMMARY OF THE INVENTION

An object of the present invention is to provide an analyzer enabling the user to hardly breathe in a malodor given off from a reagent when exchanging a reagent container.

Another object of the present invention is to provide a reagent container enabling the user to hardly breathe in a malodor given off from a reagent stored therein when exchanging the reagent container.

In order to attain the aforementioned objects, an analyzer according to a first aspect of the present invention, connected with a reagent container including a flexible container body storing a reagent, comprises an analyzer body analyzing an analyte with the reagent and reagent transporter having a first end connected to the analyzer body and a second end connected to the reagent container. The reagent transporter includes a first connectional part, detachably connected to the reagent container, having a first switching member forming and blocking a first passage between the analyzer body and the reagent container. The first switching member blocks the first passage when the first connectional part is separated from the reagent container, and forms the first passage when the first connectional part is connected to the reagent container.

As hereinabove described, the analyzer according to the first aspect is provided with the first connectional part having the first switching member forming and blocking the first passage between the analyzer body and the reagent container while the first switching member is so structured as to block the first passage when the first connectional part is separated from the reagent container and form the first passage when the first connectional part is connected to the reagent container, whereby the first switching part blocks the first passage between the analyzer body and the reagent container when the first connectional part is separated from the reagent container for exchanging the reagent container and hence the reagent partially remaining in the reagent container and the reagent transporter can be inhibited from coming into contact with the air when the reagent container is exchanged. Even if the reagent gives off a malodor when coming into contact with the air, therefore, the user of the analyzer hardly breathes in such a malodor when exchanging the reagent container.

In the aforementioned-analyzer according to the first aspect, the first switching member preferably moves to a position for blocking the first passage with the urging force of a first elastic member when the first connectional part is separated from the reagent container, and preferably moves to an opposite direction against the urging force of the first elastic member for forming the first passage when the first connectional part is connected to the reagent container. According to this structure, the first switching member can automatically block the first passage between the analyzer body and the reagent container with the urging force of the first elastic member when the first connectional part is separated from the reagent container for exchanging the reagent container.

In the aforementioned analyzer according to the first aspect, the reagent container preferably includes a second connectional part detachably connected to the first connectional part, and the first connectional part preferably includes a recess portion at least partially storing the second connectional part of the reagent container, a fixing member mounted to be capable of advancing in/retreating from the recess portion for fixing the second connectional part of the reagent container to the first connectional part and a pressing member movably mounted with respect to the recess portion for pressing the fixing member into the recess portion on a first position while canceling the pressing against the fixing member on a second position. According to this structure, the first connectional part can be easily detachably connected to the second connectional part of the reagent container by moving the pressing member to the first position and the second position.

In this case, a second elastic member preferably urges the pressing member with its urging force to locate the pressing member on the first position for pressing the fixing member. According to this structure, the first connectional part can be kept mounted/fixed on/to the second connectional part of the reagent container with the urging force of the second elastic member.

In the aforementioned analyzer according to the first aspect, the reagent transporter preferably includes a sensor for determining presence/nonpresence of the reagent in the container body. According to this structure, it is possible to easily detect that the reagent is used up and the container body must be exchanged.

In this case, the sensor preferably includes a light source part applying light to the first passage and a photodetector receiving the light from the light source part. According to this structure, presence/nonpresence of the reagent can be easily detected through the light source part and the photodetector.

In the aforementioned analyzer according to the first aspect, the reagent container preferably includes a second connectional part provided on an opening of the aforementioned flexible container body and detachably connected to the first connectional part, the second connectional part preferably includes a second switching member forming and blocking a second passage between the reagent transporter and the container body, and the second switching member preferably blocks the second passage when the second connectional part is separated from the first connectional part, and preferably forms the second passage when the second connectional part is connected to the first connectional part. According to this structure, the second switching member blocks the second passage between the reagent transporter and the container body when the second connectional part is separated from the first connectional part for exchanging the reagent container, whereby the reagent partially remaining in the container body can be inhibited from coming into contact with the external air when the reagent container is exchanged. Even if the reagent gives off a malodor when coming into contact with the air, therefore, the user hardly breathes in such a malodor.

A reagent container according to a second aspect of the present invention, detachably connected to a second end of reagent transporter of an analyzer comprising an analyzer body analyzing an analyte and the reagent transporter having a first end connected to the analyzer body for transporting a reagent to the analyzer body, comprises a flexible container body storing the reagent and a connectional part provided on an opening of the container body and detachably connected to the reagent transporter. The connectional part includes a switching member forming and blocking a passage between the reagent transporter and the container body, and the switching member blocks the passage when the connectional part is separated from the reagent transporter, and forms the passage when the connectional part is connected to the reagent transporter.

As hereinabove described, the reagent container according to the second aspect is provided with the connectional part including the switching member forming and blocking the passage between the reagent transporter and the container body while the switching member is so structured as to block the passage when the connectional part is separated from the reagent transporter and form the passage when the connectional part is connected to the reagent transporter, whereby the switching part blocks the passage between the reagent transporter and the container body when the connectional part is separated from the reagent transporter of the analyzer for exchanging the reagent container and hence the reagent partially remaining in the container body can be inhibited from coming into contact with the external air when the reagent container is exchanged. Even if the reagent gives off a malodor when coming into contact with the air, therefore, the user of the reagent container hardly breathes in such a malodor when exchanging the container body.

In the aforementioned reagent container according to the second aspect, the switching member preferably moves to a position for blocking the passage with the urging force of an elastic member when the connectional part is separated from the reagent transporter, and preferably moves to an opposite direction against the urging force of the elastic member for forming the passage when the connectional part is connected to the reagent transporter. According to this structure, it is possible to automatically block the passage between the container body and the reagent transporter with the urging force of the elastic member when the reagent transporter is separated from the container body for exchanging the reagent container.

In the aforementioned reagent container according to the second aspect, the container body preferably includes a flexible tube connected to the connectional part therein. According to this structure, it is possible to deform the tube in response to the degree of contraction of the flexible container body, whereby the reagent can be easily transported to the reagent transporter through the tube also when the volume of the reagent remaining in the container body is reduced. In this case, the container body includes an anchor, mounted on the forward end of the tube, having a hole for sucking the reagent. According to this structure, the forward end of the tube can be regularly positioned on the bottom of the container body while the reagent can be sucked through the hole of the anchor.

The aforementioned reagent container according to the second aspect preferably further comprises a box storing the container body. According to this structure, the aforementioned box can inhibit the flexible container body storing reagent from damage caused by external force.

In the aforementioned reagent container according to the second aspect, the reagent preferably includes a reagent hemolyzing blood cells. Such a reagent hemolyzing blood cells may give off a malodor when coming into contact with the air. With the reagent container according to the present invention, however, the user hardly breathes in such a malodor when exchanging the reagent container.

In the aforementioned reagent container according to the second aspect, the flexible container body preferably consists of a bag contracting in response to the residual quantity of the reagent. According to this structure, the container body may be provided with no air hole, whereby the reagent stored in the container body can be more reliably prevented from coming into contact with the air.

The aforementioned reagent container according to the second aspect preferably further comprises the reagent stored in the container body.

A reagent container according to a third aspect of the present invention, detachably connected to an analyzer, comprises a container body storing a reagent, and a connectional part for opening and closing the container body, being detachably connected to the analyzer. The connectional part closes the container body when the connectional part is separated from the analyzer, and opens the container body when the connectional part is connected to the analyzer.

As hereinabove described, the reagent container according to the third aspect is provided with the connectional part for opening and closing the container body while the connectional part is so structured as to close the container body when the connectional part is separated from the analyzer and to open the container body when the connectional part is connected to the analyzer, whereby the connectional part blocks the passage between the analyzer and the container body when the connectional part is separated from the analyzer for exchanging the reagent container and hence the reagent partially remaining in the container body can be inhibited from coming into contact with the external air when the reagent container is exchanged. Even if the reagent gives off a malodor when coming into contact with the air, therefore, the user of the reagent container hardly breathes in such a malodor when exchanging the container body.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

An embodiment of the present invention is now described with reference to the drawings.

First, the overall structures of a blood cell analyzer and a reagent container according to the embodiment of the present invention are described with reference to FIG. 1. In this embodiment, the analyzer and the reagent container according to the present invention are applied to the blood cell analyzer and the reagent container employed for this blood cell analyzer. The reagent container stores a reagent for hemolyzing red blood cells employed for measuring immature white blood cells in the blood cell analyzer according to this embodiment.

Figure 1:
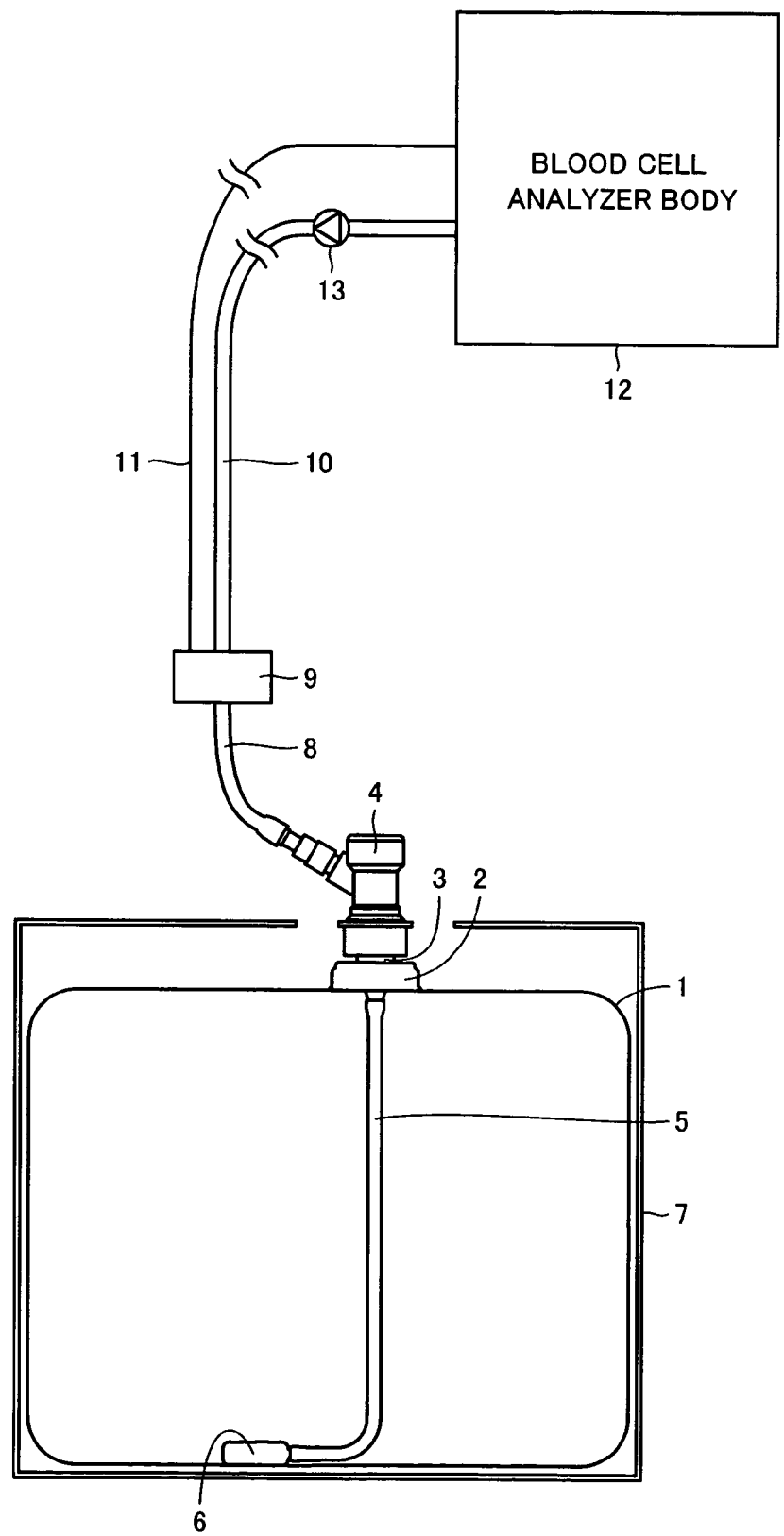
FIG. 1 schematically illustrates the overall structures of a blood cell analyzer and a reagent container according to an embodiment of the present invention.
Figure 2:
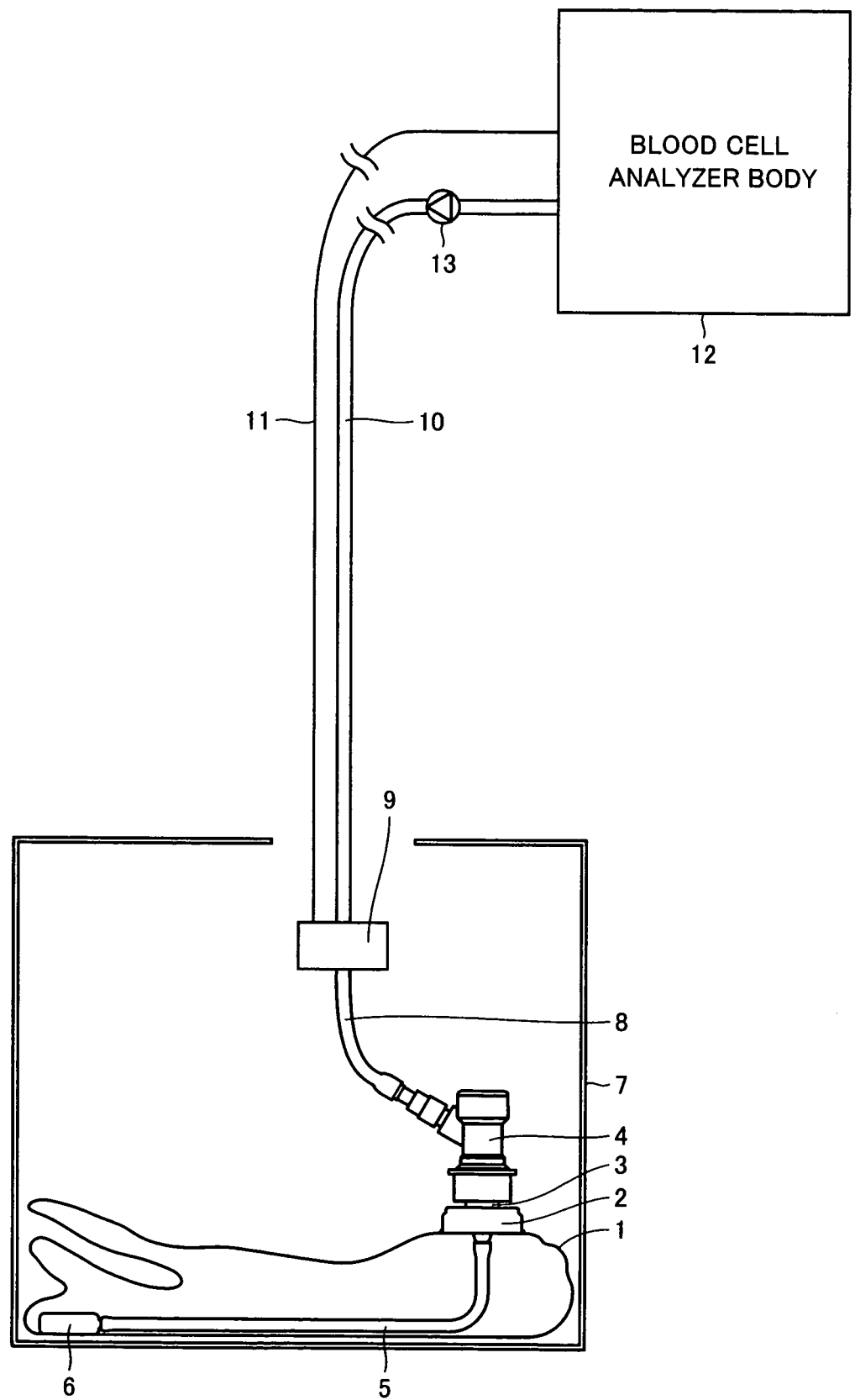
FIG. 2 schematically illustrates a contracting container body of the reagent container according to the embodiment shown in FIG. 1.

According to this embodiment, the blood cell analyzer body 12 and a container body 1 consisting of a flexible bag for storing the reagent for hemolyzing red blood cells are connected with each other through flexible tubes 8 and 10 of silicon, as shown in FIG. 1. As the reagent is sucked from the container body 1 and the volume thereof is reduced, the container body 1 contracts as shown in FIG. 2 without incorporating the outside air. The forward end of the tube 8 is connected to a socket 4, which in turn is connected to a plug 3. The plug 3 is mounted on the container body 1 through a cap screw 2. Still another flexible tube 5 of silicon is arranged in the container body 1 for sucking the reagent. The tube 5 has a first end connected to the plug 3 and a second end mounted with an anchor 6 of resin. This anchor 6 is provided for regularly positioning the forward end of the tube 5 on the bottom of the container body 1.

A bubble sensor 9 is arranged between the tubes 8 and 10, in order to detect presence/nonpresence of the reagent supplied from the tube 8 to the tube 10. A power supply line 11 from the blood cell analyzer body 12 is connected to the bubble sensor 9. The tube 10 is provided with a check valve 13 for preventing the reagent from regurgitating from the blood cell analyzer body 12 to the tube 10. The container body 1 of the reagent container is stored in a corrugated fiberboard box 7.

The structures of the cap screw 2, the plug 3, the socket 4, the tube 5 and the anchor 6 are now described in detail with reference to FIGS. 3 to 7.

Figure 3:
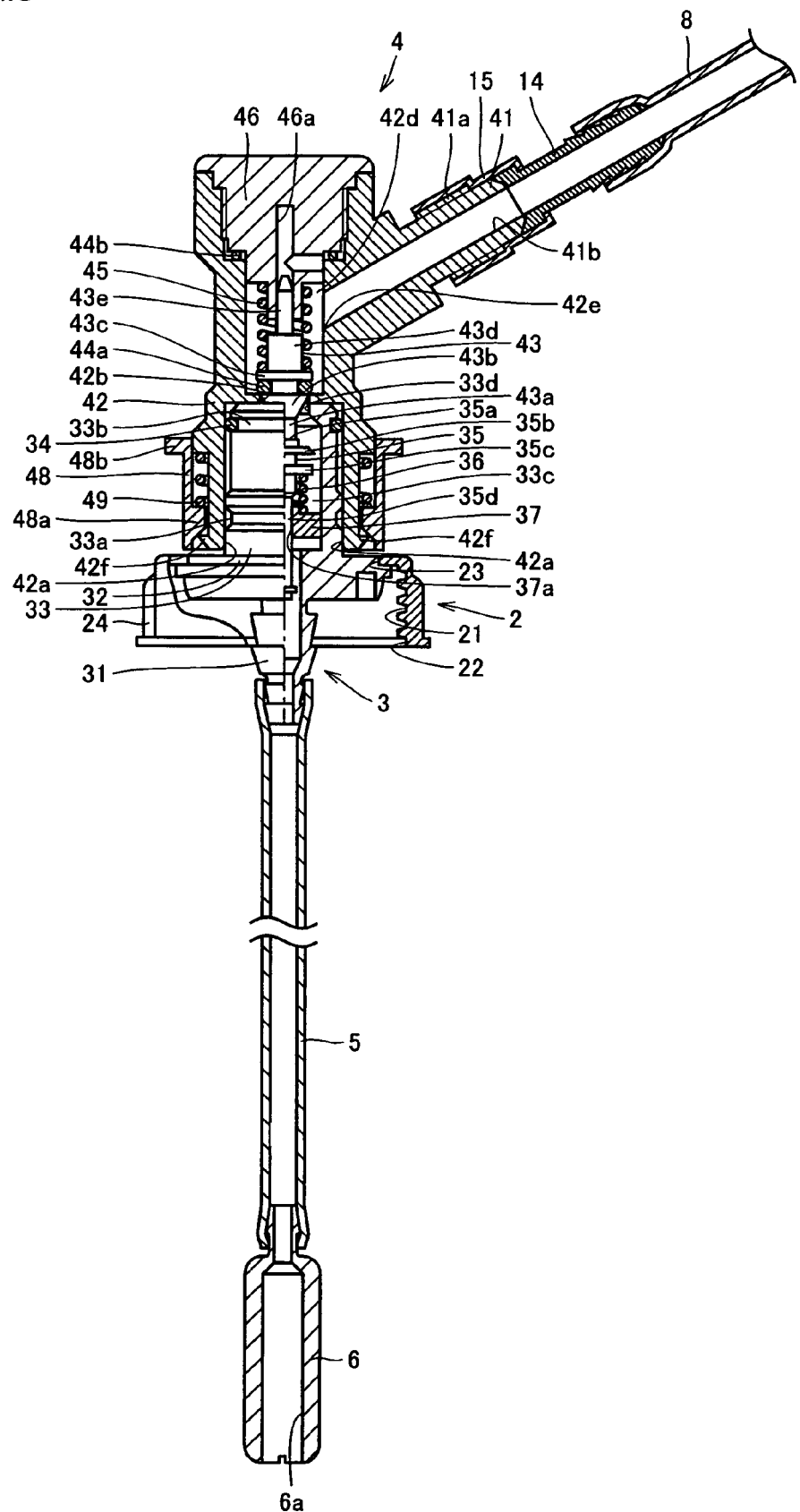
FIG. 3 is a partially fragmented sectional view showing the structure of a connectional part between the blood cell analyzer and the reagent container according to the embodiment shown in FIG. 1 in detail.
Figure 4:
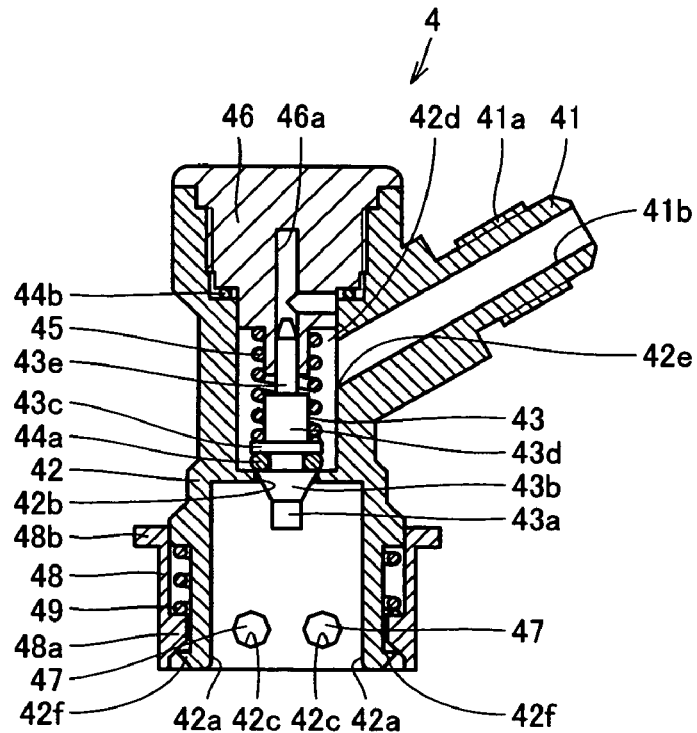
FIG. 4 is a partially fragmented sectional view showing a socket employed for the connectional part according to the embodiment shown in FIG. 3.

As shown in FIGS. 3 and 4, the socket 4 includes a connectional part 41, a body part 42 of resin, a switching member 43 of resin, O-rings 44a and 44b of rubber, a helical compression spring 45 of a metal, a lid member 46 of resin, balls 47 of a metal, a pressing member 48 of resin and another helical compression spring 49 of a metal. The connectional part 41 is provided with a screw part 41a and a reagent supply hole 41b. A tube joint member 14 of a metal is mounted on the forward end of the connectional part 41. The tube joint member 14 is fixed by fitting a fixing nut 15 with the screw part 41a of the connectional part 41. The tube 8 is engaged with the forward end of the tube joint member 14.

Figure 5:
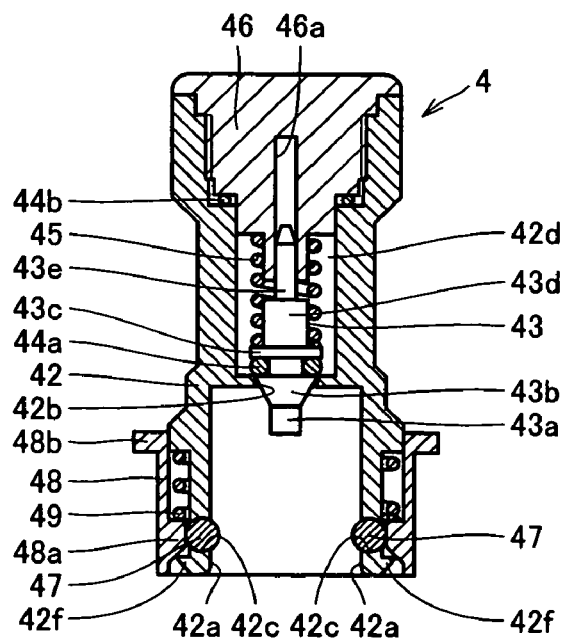
FIG. 5 is a sectional view of the socket shown in FIG. 4 taken along a portion provided with balls.

As shown in FIGS. 3 to 5, the body part 42 of the socket 4 is provided with a recess portion 42a for receiving the plug 3. A void 42d is provided above the recess portion 42a through a passage forming hole 42b. A switching member 43 of resin is vertically movably arranged in the passage forming hole 42b and the void 42d. In other words, the switching member 43 is arranged to be movable between a lower position for closing the passage forming hole 42b and blocking a passage and an upper position for opening the passage forming hole 42b and forming the passage.

A cylindrical forward end 43a of the switching member 43 closer to the void 42a comes into contact with the plug 3, as shown in FIG. 3. The switching member 43 is also provided with a tapered part 43b continuous with the forward end 43a. The tapered part 43b has a shape capable of blocking the passage forming hole 42b. The aforementioned O-ring 44a of rubber is arranged between the tapered part 43b and a flange part 43c. This O-ring 44a has a function of preventing the reagent from leaking from the passage forming hole 42b blocked with the tapered part 43b toward the void 42a. The switching member 43 is further provided with a barrel 43d continuous with the flange part 43c and a forward end 43e, closer to the lid member 46 and continuous with the barrel 43d, having a smaller diameter than the barrel 43d. The forward end 43e closer to the lid member 46 is vertically movably inserted in an insertion hole 46a of the lid member 46. The aforementioned helical compression spring 45 is arranged between the flange part 43c and the lid member 46. This helical compression spring 45 is arranged to urge the tapered part 43b of the switching member 43 and the O-ring 44a to the lower position for closing the passage forming hole 42b. The O-ring 44b is arranged between the lower surface of the lid member 46 arranged in the void 42d of the body part 42 and the body part 42, in order to prevent the reagent from leaking from between the lid member 46 and the body part 42. The body part 42 is provided with a hole 42e for connecting the void 42d and the supply hole 41b of the connectional part 41 with each other.

Ball retention holes 42c are provided on prescribed portions of the recess portion 42a of the body part 42. The aforementioned balls 47 of a metal are mounted in the ball retention holes 42c to be able to advance in/retreat from the recess portion 42a. The ball retention holes 42c have octagonal openings, and the balls 47 have diameters incapable of passing through the ball retention holes 42c. The balls 47 are arranged between the body part 42 and the pressing member 48, not to drop also when the socket 4 is detached from the plug 3. While the ball retention holes 42c may alternatively have circular openings, polygonal openings capable of preventing the balls 47 from anchoring to the ball retention holes 42c, are more preferable. The aforementioned pressing member 48 is provided outside the position of the body part 42 formed with the recess portion 42a, in order to press the balls 47 into the recess portion 42a. This pressing member 48 presses the balls 47 when located on a lower position while canceling the pressing against the balls 47 when located on an upper position. The pressing member 48 is provided with a grip part 48b easily graspable for vertically moving the pressing member 48. The aforementioned helical compression spring 49 is provided between the outer peripheral surface of the body part 42 and the inner peripheral surface of the pressing member 48, in order to urge the pressing member 48 downward. The body part 42 is further provided with a stopper 42f coming into contact with a pressing part 48a of the downwardly urged pressing member 48. In a normal state, the pressing part 48a of the pressing member 48 is arranged on the lower position for pressing the balls 47 with the urging force of the helical compression spring 49.

Figure 6:
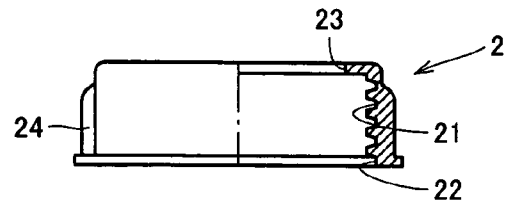
FIG. 6 is a partially fragmented sectional view showing a cap screw for fixing a plug and the reagent container according to the embodiment shown in FIG. 3 to each other.

As shown in FIGS. 3 and 6, the cap screw 2 includes a screw part 21 formed on its inner surface, a lower hole 22, an upper hole 23 and a protruding portion 24 formed on its outer side surface.

Figure 7:
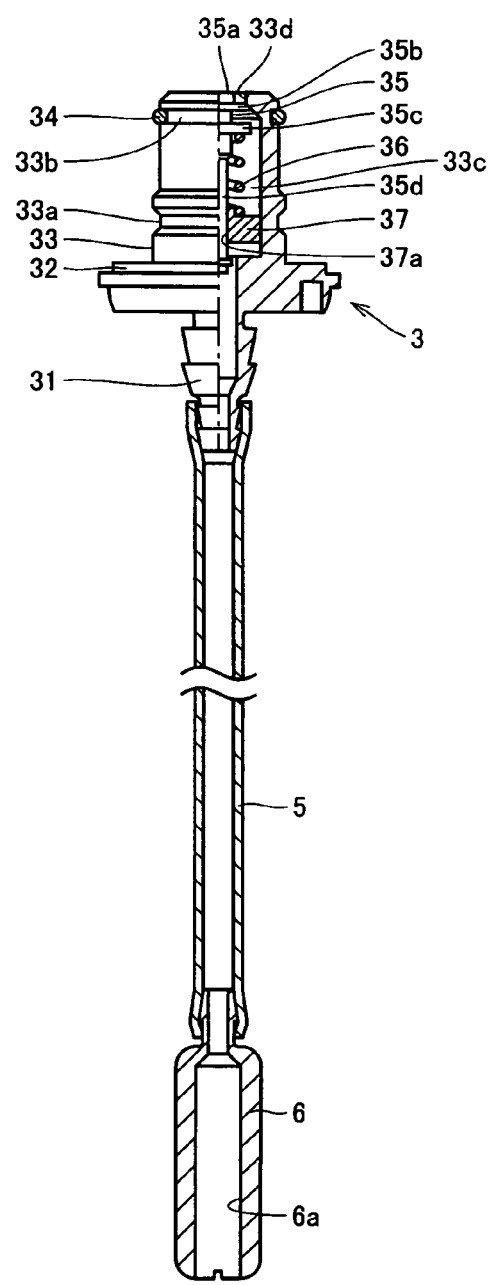
FIG. 7 is a partially fragmented sectional view showing the plug, a tube and an anchor according to the embodiment shown in FIG. 3.

As shown in FIGS. 3 and 7, the plug 3 includes a tube joint part 31, a flange part 32, an insertion part 33, an O-ring 34 of rubber, a switching member 35, a helical compression spring 36 of a metal and a support part 37. The tube joint part 31, the flange part 32, the insertion part 33 and the support part 37 are made of resin such as polyethylene or polyacetal. The switching member 35 consists of thermoplastic polyester elastomer such as Hytrel by Du Pont-Toray Co., Ltd., for example. This thermoplastic polyester elastomer has intermediate softness between those of rubber and plastic.

The tube joint part 31 of the plug 3 is constituted of a plurality of tapered parts capable of connecting the tube 5. The flange part 32 is formed to be integrally continuous with the tube joint part 31. As shown in FIG. 3, the flange part 32 is engaged with the upper hole 23 of the cap screw 2. The insertion part 33 is formed to be integrally continuous with the flange part 32. As shown in FIG. 3, the insertion part 33 is inserted into the recess portion 42a of the body part 42 of the socket 4. The insertion part 33 is provided with a fixing groove 33a and an O-ring receiving groove 33b. The fixing groove 33a has a width smaller than the outer diameter of the balls 47 of the socket 4, and both ends of this fixing groove 33a closer to an opening are chamfered. The aforementioned O-ring 34 of rubber is arranged in the O-ring receiving groove 33b. As shown in FIG. 3, this O-ring 34 is provided for preventing the reagent from leaking from the recess portion 42a when the insertion part 33 of the plug 3 is inserted in the recess portion 42a of the socket 4.

The plug 3 is provided therein with a void 33c and a passage forming hole 33d formed above the void 33c. The void 33c is provided therein with the aforementioned support part 37 having a hole 37a vertically movably receiving a shank 35d of the aforementioned switching member 35. In other words, the switching member 35 is movable between a position for closing the passage forming hole 33d and blocking a passage and a position for opening the passage forming hole 33d and forming the passage. The switching member 35 is provided on its upper end with a contact part 35a coming into contact with the forward end 43a of the switching member 43 of the socket 4. A tapered part 35b is formed to be continuous with the contact part 35a. This tapered part 35b has a shape capable of blocking the passage forming hole 33d from inside. The switching member 35 is also provided with a flange part 35c. The helical compression spring 36 is arranged between the flange part 35c and the support part 37. The helical compression spring 36 has a function of urging the tapered part 35b to block the passage forming hole 33d.

As shown in FIG. 3, the anchor 6 of resin connected to an end of the tube 5 is provided with a hole 6a for sucking the reagent.

Figure 8:
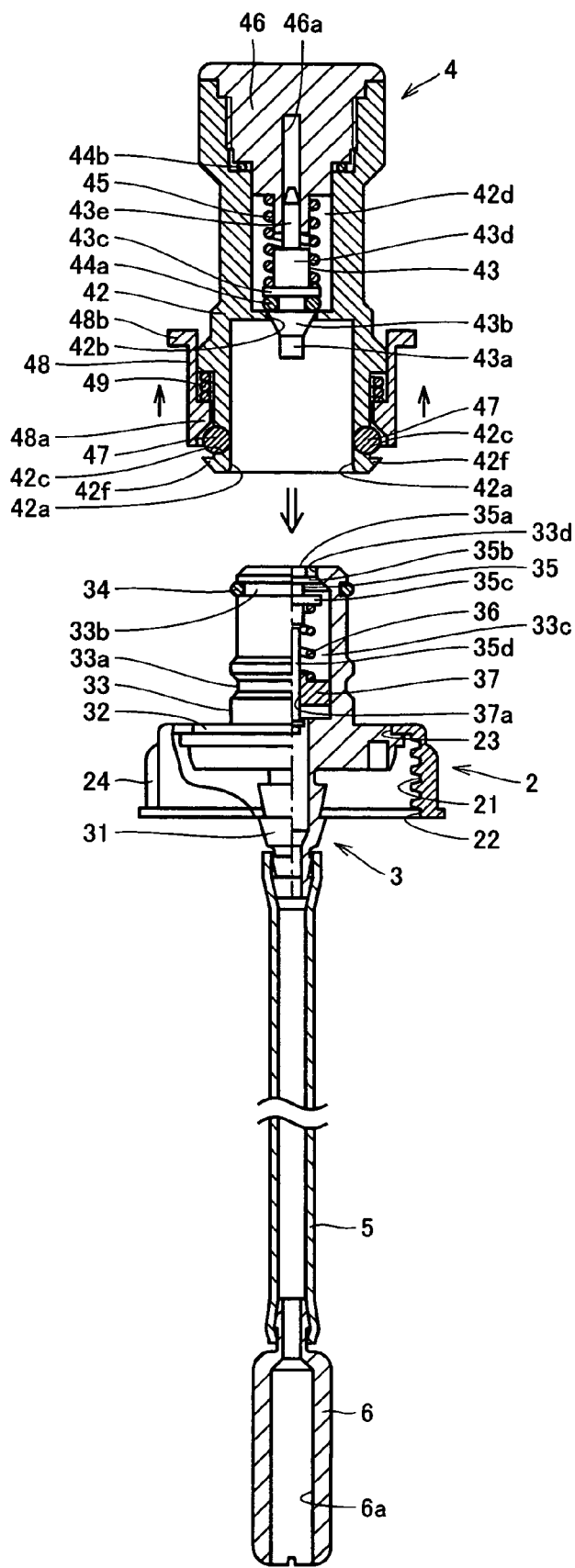
FIGS. 8, 9 and 10 are partially fragmented sectional views for illustrating an operation of connecting the socket and the plug according to the embodiment shown in FIG. 3 with each other.

An operation of attaching/detaching the socket 4 to/from the plug 3 mounted on the container body 1 through the cap screw 2 is now described with reference to FIGS. 8 to 10. In order to attach the socket 4 to the plug 3, the pressing member 48 of the socket 4 is moved upward as shown in FIG. 8. At this time, the pressing member 48 can be easily elevated by grasping the grip part 48b of the pressing member 48. Thus, the balls 47 are released from the pressing by the pressing part 48a of the pressing member 48, to be outwardly retreated from the recess portion 42a.

Figure 9:
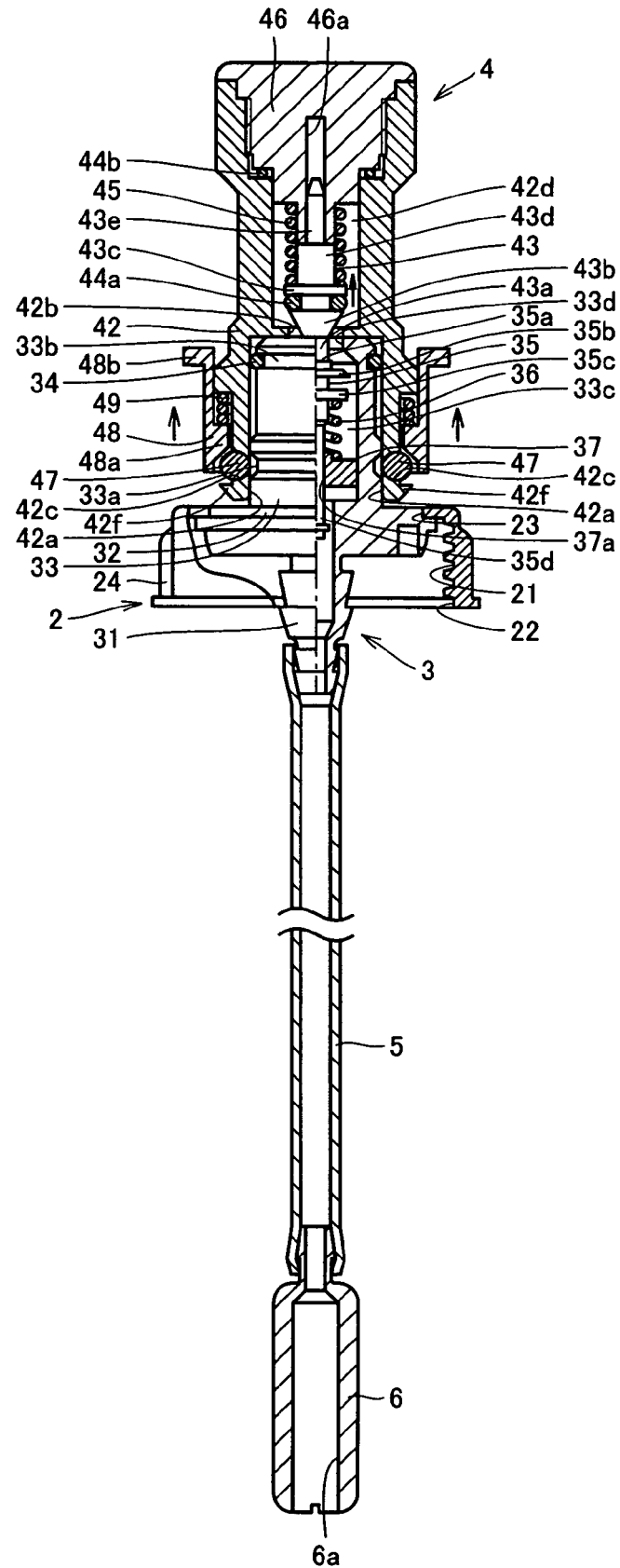

The recess portion 42a of the socket 4 is engaged with the insertion part 33 of the plug 3 while the pressing member 48 is elevated in the aforementioned manner, to attain the state shown in FIG. 9. In the state shown in FIG. 9, the contact part 35a of the switching member 35 of the plug 3 is pushed down by the forward end 43a of the switching member 43 of the socket 4 while the forward end 43a of the switching member 43 of the socket 4 is pushed up due to reaction from the contact part 35a of the switching member 35 of the plug 3. Thus, both of the passage forming holes 42b and 33d of the socket 4 and the plug 3 are opened to form the passages. In the state shown in FIG. 9, further, the O-ring 34 mounted on the insertion part 33 of the plug 3 comes into close contact with the inner surface of the recess portion 42a of the socket 4, thereby preventing the reagent from leaking from the recess portion 42a.

Figure 10:
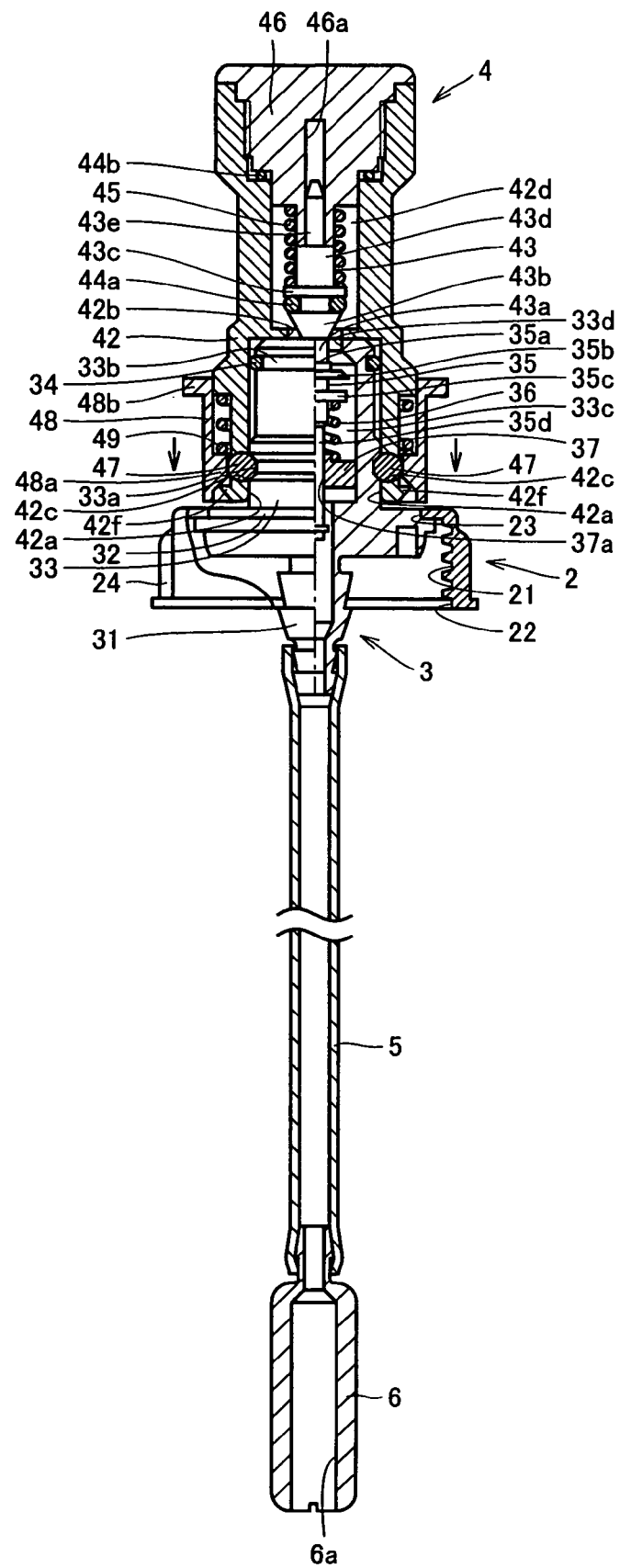

From the state shown in FIG. 9, the pressing member 48 is returned downward for urging the helical compression spring 49 as shown in FIG. 10, so that the pressing part 48a of the pressing member 48 externally presses the balls 47 inward. Thus, the balls 47 move into the recess portion 42a to engage with the fixing groove 33a of the insertion part 33 of the plug 3, thereby fixing the plug 3 and the socket 4 to each other. Thus, the socket 4 is attached to the plug 3.

In order to exchange the container body 1 when the reagent stored therein is used up, the socket 4 is detached from the plug 3 contrarily to the above attaching operation. In this case, the grip part 48b of the pressing member 48 is elevated from the state shown in FIG. 10 thereby moving up the pressing member 48 as shown in FIG. 9, for extracting the socket 4 upward from the plug 3. Thus, the switching member 35 of the plug 3 closes the passage forming hole 33d with the urging force of the helical compression spring 36 while the switching member 43 of the socket 4 also closes the passage forming hole 42b with the urging force of the helical compression spring 45, as shown in FIG. 8. When the socket 4 is detached from the plug 3 for exchanging the container body 1 in the aforementioned manner, the passages are so quickly blocked that the reagent partially remaining in the container body 1 or the tube 8 is inhibited from coming into contact with the air.

Figure 11:
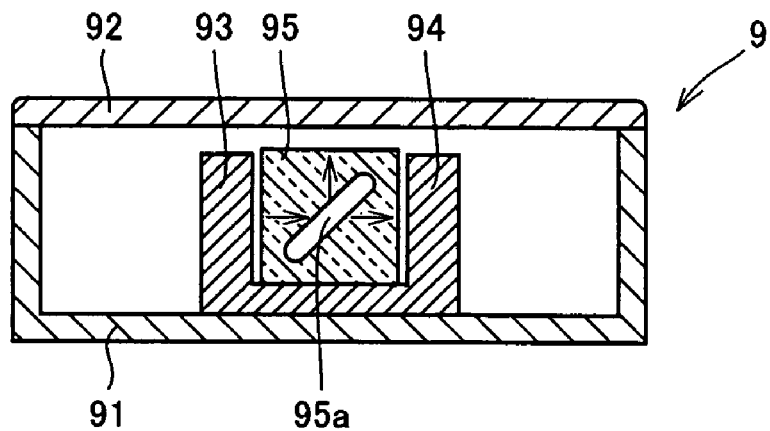
FIG. 11 is a sectional view showing a bubble sensor according to the embodiment shown in FIG. 1.
Figure 12:
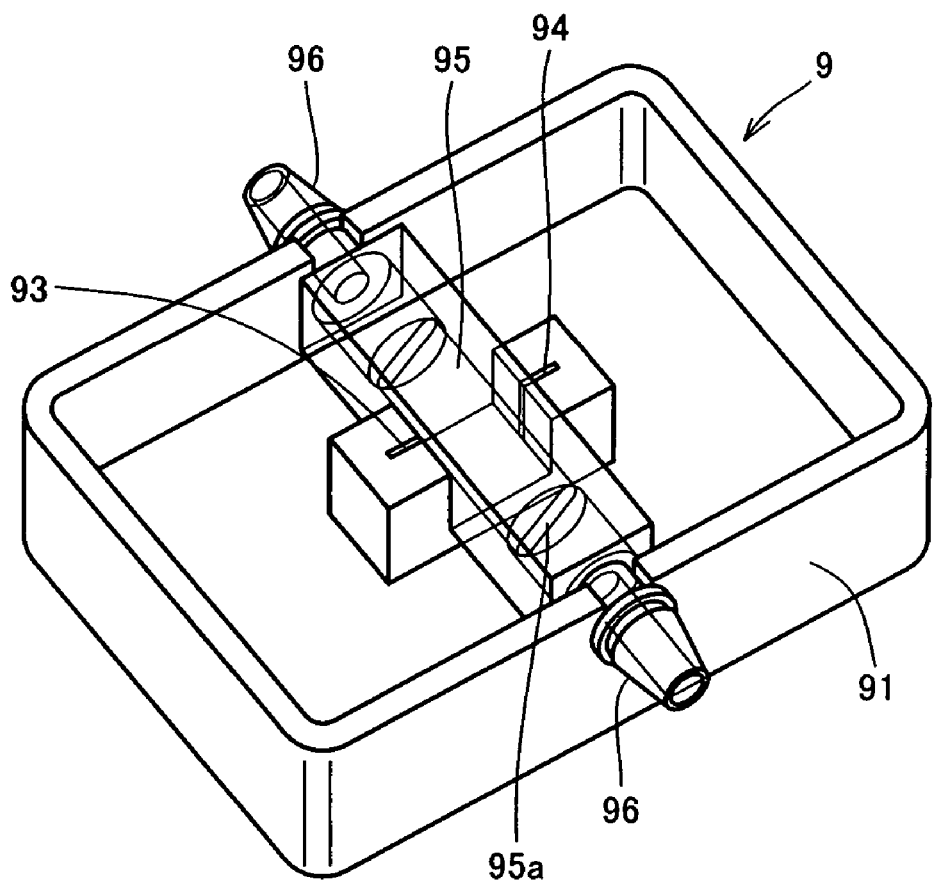
FIG. 12 is a perspective view showing an unlidded state of the bubble sensor shown in FIG. 11.

The bubble sensor 9 shown in FIG. 1 is now described in detail with reference to FIGS. 11 and 12. In the bubble sensor 9 shown in FIGS. 11 and 12, a light-emitting diode 93 and a photodetector 94 are oppositely arranged in a case 91 of resin at a prescribed interval. A square pole-shaped light-transmittable transparent member 95 having an elongated passage 95a is arranged between the light-emitting diode 93 and the photodetector 94. Joint members 96 are provided on both ends of the transparent member 95, in order to connect the tubes 8 and 10 (see FIG. 1) with the bubble sensor 9. A lid 92 is mounted on the upper portion of the case 91.

A method of detecting presence/nonpresence of the reagent flowing through the passage 95a with the light-emitting diode 93 and the photodetector 94 is described with reference to FIG. 11. When no reagent is present in the passage 95a, light emitted from the light-emitting diode 93 is reflected upward, and hence the photodetector 94 receives no light from the light-emitting diode 93. When the reagent flows is present in the passage 95a, on the other hand, the light emitted from the light-emitting diode 93 is straightforwardly transmitted through the passage 95a. Thus, the photodetector 94 receives the light from the light-emitting diode 93. Therefore, whether or not the reagent is present in the passage 95a is determined by determining whether or not the photodetector 94 receives the light from the light-emitting diode 93. If the photodetector 94 receives no light from the light-emitting diode 93 although the blood cell analyzer body 12 operates to suck the reagent from the container body 1, it is determined that the reagent stored in the container body 1 is used up.

According to this embodiment, the socket 4 is provided with the switching member 43 blocking the passage when the socket 4 is separated from the plug 3 while forming the passage when the socket 4 is connected with the plug 3 and the plug 3 is provided with the switching member 35 blocking the passage when the plug 3 is separated from the socket 4 while forming the passage when the plug 3 is connected with the socket 4 as described above. When the socket 4 is separated from the plug 3 mounted on the container body 1 for exchanging the container body 1, therefore, the passages are so blocked that the reagent partially remaining in the container body 1 and the tube 8 can be inhibited from coming into contact with the air. Also in this embodiment employing the reagent for hemolyzing blood cells, giving off a malodor when coming into contact with the air, therefore, the user hardly breathes in such a malodor when exchanging the container body 1.

According to this embodiment, as hereinabove described, the switching member 43 of the socket 4 is so structured as to block the passage with the urging force of the helical compression spring 45 while the switching member 35 of the plug 3 is also so structured as to block the passage with the urging force of the helical compression spring 36, whereby the passages formed between the plug 3 and the socket 4 can be automatically blocked with the urging force of the helical compression springs 36 and 45 when the socket 4 is detached from the plug 3 mounted on the container body 1.

According to this embodiment, further, the pressing member 48 is so provided on the socket 4 as to press the balls 47 on the lower position and cancel the pressing against the balls 47 on the upper position as hereinabove described, whereby the socket 4 can be easily detachably connected to the plug 3. In addition, the socket 4 can be easily kept attached and fixed to the plug 3 by urging the pressing member 48 to the lower position for pressing the balls 47 with the urging force of the helical compression spring 49.

According to this embodiment, further, the bubble sensor 9 detecting presence/nonpresence of the reagent is provided for detecting presence/nonpresence of the reagent in the passage 95a as hereinabove described, whereby it is possible to easily detect that the reagent stored in the container body 1 is used up and the container body 1 must be exchanged.

According to this embodiment, further, the flexible tube 5 is arranged in the container body 1 as hereinabove described, whereby the tube 5 can be deformed in response to the degree of contraction of the flexible container body 1 so that the reagent can be easily sucked through the tube 5 also when the volume of the reagent stored in the container body 1 is reduced. In addition, the anchor 6 having the hole 6a for sucking the reagent is mounted on the forward end of the tube 5, so that the forward end of the tube 5 can be regularly positioned on the bottom of the container body 1 and the reagent can be sucked through the hole 6a of the anchor 6.

According to this embodiment, further, the container body 1 is arranged in the corrugated fiberboard box 7 as hereinabove described, whereby the flexible container body 1 storing the reagent can be inhibited from damage caused by external force.

According to the aforementioned embodiment, further, the container body 1 is constituted of the bag contracting in response to the residue of the reagent so that the container body 1 may be provided with no air hole as hereinabove described, whereby the reagent stored in the container body 1 can be further reliably prevented from coming into contact with the air.

Although the present invention has been described and illustrated in detail, it is clearly understood that the same is by way of illustration and example only and is not to be taken by way of limitation, the spirit and scope of the present invention being limited only by the terms of the appended claims.

For example, while the above embodiment has been described with reference to the blood cell analyzer body 12 serving as an exemplary analyzer body, the present invention is not restricted to this but is also applicable to an analyzer body, other than the blood cell analyzer body 12, employing a reagent. In particular, the present invention is effective for employing a reagent giving off a malodor when coming into contact with the air.

While the bubble sensor 9 consists of the light-emitting diode 93 and the photodetector 94 in the aforementioned embodiment, the present invention is not restricted to this but another sensor capable of detecting presence/nonpresence of a reagent may alternatively be employed.

While the balls 47 are employed for fixing the plug 3 and the socket 4 to each other in the aforementioned embodiment, the present invention is not restricted to this but a similar effect can also be attained by employing fixing members having shapes other than those of balls.

What is claimed is:

1. An analyzer connected with a reagent container that comprises a flexible container body configured for storing a reagent, the analyzer comprising:
    an analyzer body configured for analyzing an analyte with said reagent; and
    a reagent transporter configured for connecting said analyzer body and said reagent container via a passageway in fluid communication with said analyzer body and said container body, said reagent transporter comprising:
    a tube connected to said analyzer body at one end; and
        a first connector detachably connected to a second connector, said first connector comprising a tube connecting part connected to the other end of said tube, a first connecting part, a first passageway in fluid communication with said tube and said first connecting part, a first switching member blocking said first connector passageway, and a first elastic member creating an urging force to make said first switching member block said first connector passageway, and
        a second connector comprising a container connecting part connected to said container body, a second connecting part connected to said first connecting part, a second connector passageway in fluid communication with said container connecting part and said second connecting part, a switching member blocking said second container passageway, and a second elastic member creating an urging force to make said second switching member block said second connector passageway, wherein said first switching member blocks said first connector passageway by moving said first switching member with an urging force of said first elastic member when said first and second connectors are decoupled, wherein said second switching member blocks said second connector passageway by moving said second switching member with an urging force of said second elastic member when said first and second connectors are decoupled, and wherein when said first and second connectors are connected, said first and second switching members push against each other in opposite directions against said urging forces of said first and second elastic members, thereby releasing the blocking of said first and second connector passageways to form said passageway.

2. The analyzer according to claim 1, wherein said first connector further comprises:

a recess portion at least partially receiving said second connectional part of said reagent container;

a fixing member mounted to be capable of advancing in and retreating from said recess portion for fixing said second connector to said first connectional part; and a pressing member movably mounted with respect to said recess portion for pressing said fixing member into said recess portion in a first position while canceling the pressing against said fixing member in a second position.

3. The analyzer according to claim 2, wherein a second elastic member urges said pressing member with its urging force to locate said pressing member in said first position for pressing said fixing member.

4. The analyzer according to claim 1, wherein said reagent transporter further comprises a sensor for determining the presence and nonpresence of said reagent in said tube.

5. The analyzer according to claim 4, wherein said sensor comprises a light source part applying light to said tube and a photodetector receiving said light from said light source part.

* * * * *